(12) United States Patent
Mayo-Alvarez et al.

(10) Patent No.: US 7,192,966 B2
(45) Date of Patent: Mar. 20, 2007

(54) PHARMACEUTICAL COMPOSITION

(75) Inventors: Ricardo Mayo-Alvarez, Miami, FL (US); Ronny McNeil, Chattanooga, TN (US)

(73) Assignee: Branded Products for the Future, Chattancoga, TN (US)

( * ) Notice: Subject to any disclaimer, the term of this patent is extended or adjusted under 35 U.S.C. 154(b) by 0 days.

(21) Appl. No.: 10/716,163

(22) Filed: Nov. 17, 2003

(65) Prior Publication Data

US 2004/0151791 A1    Aug. 5, 2004

Related U.S. Application Data

(60) Provisional application No. 60/426,867, filed on Nov. 15, 2002.

(51) Int. Cl.
*A61K 31/44* (2006.01)
*A61K 8/365* (2006.01)
*A61K 31/74* (2006.01)
*A61K 31/77* (2006.01)

(52) U.S. Cl. .................... 514/282; 514/892; 424/55; 424/78.01; 424/78.13

(58) Field of Classification Search ............... 424/738, 424/78.01, 165; 514/282, 892
See application file for complete search history.

(56) References Cited

U.S. PATENT DOCUMENTS

| | | | |
|---|---|---|---|
| 3,980,766 A * | 9/1976 | Shaw et al. | |
| 4,181,719 A * | 1/1980 | Margetts et al. | 514/162 |
| 4,366,159 A * | 12/1982 | Magruder | |
| 4,599,342 A * | 7/1986 | LaHann | 514/282 |
| 4,762,709 A * | 8/1988 | Sheumaker | |
| 4,999,200 A | 3/1991 | Casillan | |
| 5,232,699 A * | 8/1993 | Colliopoulos | 424/738 |
| 5,516,524 A * | 5/1996 | Kais et al. | 424/439 |
| 5,849,240 A * | 12/1998 | Miller et al. | 264/460 |
| 6,284,274 B1 | 9/2001 | Merrill et al. | |
| 6,375,957 B1 * | 4/2002 | Kaiko et al. | 424/400 |

FOREIGN PATENT DOCUMENTS

| GB | 2 281 204 A | 3/1995 |
|---|---|---|
| GB | 2281205 A * | 3/1995 |

OTHER PUBLICATIONS

Lazarus H et al., Hospice Journal, 1990, 6(4): 1-15. A multi-investigator clinical evaluation of oral controlled-release morphine (MS Contin [Registered Trademark] Tablets) administered to cancer patients.*

Raeder J C et al., Anesthesia & Analgesia, 2001, 92(6): 1470-1472. Oral ibuprofen versus paracetamol plus codeine for analgesia after ambulatory surgery, Abstract.*

Mullican, W S et al., Clinical Therapeutics, (Sep. 2001), 23(9): 1429-1445. Tramadol/acetaminophen combination tablets and codeine/acetaminophen combination capsules for the management of chronic pain: A comparative trial, Abstract.*

Marketletter, (Jul. 7, 1997), US seniors surveyed on pain relief, pp N/A. An excerpt.*

Maurer A H et al., J of Nuclear Medicine (May 1996), 37(5): 818-822. Opioid and opioid-like drug effects on whole-gut transit measured by scintigraphy, Abstract.*

Rauck R L et al., Current Therapeutic Research-Clinical and Experimental, (Dec. 1994), 55(4): 1417-1431. Comparison of tramadol and acetaminophen in elderly patients, Abstract.* http://www.drugs.com/PDR/Senokot_Tablets.html (Jul. 25, 2004). Drugs.com (trademark). PDR Drug Information of SENOKOT-S(registered trademark) Tablets (standardized senna concentrate and docusate sodium) Natural Vegetable Laxative/Stool Softener Combination.*

Persaud et al.Current Medical Research & Opinion(1985), 9(9):626-633. The relative bioavailibility of paracetarnol & codeine after oral administration of buclizine, paracetamol & codeine, with or without docusate, & or paracetamol alone in healthy volunteers.*

Herndon, C. et al. Pharmacotherapy (Feb.-Mar. 2002), 22(2): 240-250. Management of opioid-induced gastrointestinal effects in patients receiving palliative care.*

Adam, "A Treatment for the Acute Migraine Attack"; *The Journal of International Medical Research*; 1987; 15: pp. 71-75.

Persaud et al.; "The relative bioavailability of paracetamol and codeine after oral administration of a combination of buclizine, paracetamol and codeine, with or without docusate, and of paracetamol alone in healthy volunteers"; *Current Medical Research and Opinions*; vol. 9, No. 9, 1985; pp. 626-633.

Tylox® product information page; McNeil Pharmaceutical revised Jun. 1997.

* cited by examiner

*Primary Examiner*—Michele Flood
(74) *Attorney, Agent, or Firm*—Sheridan Ross P.C.

(57) ABSTRACT

A pharmaceutical composition comprising an analgesic or analgesic combination and a stool softener is disclosed. The analgesic is selected from morphine, meperidine, fentanyl, hydromorphone, oxymorphone, oxycodone, hydrocodone, methadone, propoxyphene, pentazocine, levorphanol, codeine, acetaminophen and combinations of these analgesics. The composition is formulated for oral administration as a liquid or solid dosage form for immediate, slow, delayed or sustained-release characteristics.

8 Claims, No Drawings

PHARMACEUTICAL COMPOSITION

CROSS REFERENCE TO RELATED APPLICATIONS

This application claims priority to U.S. Provisional Application Ser. No. 60/426,867 filed Nov. 15, 2002, which is incorporated in its entirety by this reference.

FIELD OF THE INVENTION

The invention resides in the field of analgesic-based pharmaceutical compositions.

BACKGROUND OF THE INVENTION

Oral analgesics and analgesic combinations have become some of the most frequently prescribed medications for the treatment of patients experiencing both acute and chronic pain. This use has increased recently with newer and more progressive pain treatment regimens emphasizing aggressive and preventive approaches to pain management. Unfortunately, many of the available opiate and opiate-related analgesics are constipating. This adverse effect often necessitates dosage reduction or diet modification to alleviate or prevent constipation in chronic pain patients.

One method of preventing and treating constipation associated with the use of opiates and their analogs is the administration of laxatives. This measure has the advantage of preventing further complications and side effects caused by medication prescribed to a patient suffering pain that requires pharmaceutical intervention. Stool softening laxatives or bulk laxatives are typically chosen over irritant or stimulatory laxatives to alleviate constipation in these patients without adversely affecting electrolyte imbalance or digestion and absorption of other medications and foods.

Typically, patients prescribed opiate-containing analgesics on an outpatient basis are instructed to purchase and use a non-prescription stool softening product. In many instances, these patients either forget, or choose not to purchase the recommended stool softener resulting in constipation that is later more difficult to treat than to initially prevent. Additionally, those patients that do begin use of a stool softener do not vary the dose of the laxative as their opiate use increases or decreases, often resulting in constipation or diarrhea. Thus, there exists a need for a pharmaceutical dosage from incorporating opiate analgesics and analgesic combinations and a stool softener that will inherently increase or reduce the dosage of the laxative concurrently with a patient's opiate use.

SUMMARY OF THE INVENTION

The invention is directed to a pharmaceutical composition comprising an analgesic and a stool softener. The analgesic may be morphine, meperidine, fentanyl, hydromorphone, oxymorphone, oxycodone, hydrocodone, methadone, propoxyphene, pentazocine, levorphanol, codeine or combinations of these analgesics. The stool softener may be any compound known to increase the water content of the colon and thereby soften the stool. For example, it is known that laxatives traditionally thought of as bulk laxatives will function to soften the stool by increasing the water content of the stool and these bulk laxatives are therefore to be included within the term stool softener for the purposes of this disclosure. Preferably, the stool softeners for use in the pharmaceutical compositions of the present invention may be docusate, poloxamer 188, psyllium, methylcellulose, carboxymethyl cellulose, polycarbophil, bisacodyl, castor oil, magnesium citrate, magnesium hydroxide, magnesium sulfate, dibasic sodium phosphate, monobasic sodium phosphate, sodium biphosphate or combinations of these compounds. Preferably, the pharmaceutical composition comprises between about 0.10 grams to 10.0 grams of psyllium. In further embodiments of the invention, the pharmaceutical composition comprises between about 0.25 grams and about 2 grams, or between about 0.5 grams and about 5 grams of psyllium.

In a preferred embodiment of the invention, the pharmaceutical composition further comprises between about 10 mg and about 2000 mg of acetaminophen. In a more preferred embodiment of the invention, the pharmaceutical composition comprises between about 50 mg and about 1000 mg, or between about 325 mg and about 750 mg of acetaminophen.

Preferably, the pharmaceutical compositions of the present invention are formulated as single oral dosage forms such as oral solutions, oral syrups, soft gelatin capsules, hard gelatin capsules, tablets, capsules and sterile packaged powder including pharmaceutically-acceptable excipients. In another embodiment of the present invention, the pharmaceutical composition is formulated in a sustained release carrier that causes the analgesic, the stool softener or both to be released over an extended time period following oral administration to a human patient. Preferably, the time period of sustained release of the analgesic is a period of about 4 to about 16 hours or a period of about 8 to about 24 hours after being orally administered to a human patient. In another embodiment of the present invention the pharmaceutical composition comprises codeine and at least about 50 mg of docusate. This embodiment may also contain a non-opioid analgesic such as acetaminophen in a range of between about 10 mg to about 2000 mg of acetaminophen. In a preferred embodiment of the invention, the pharmaceutical composition further comprises between about 10 mg and about 2000 mg of acetaminophen. In further embodiments of the invention, the pharmaceutical composition can contain between about 50 mg and about 1000 mg, or between about 325 mg and about 750 mg of acetaminophen.

The invention also provides a method of preventing constipation during analgesic use by co-administering a stool softener with an analgesic in a single oral dosage form. The analgesic used in the method may be morphine, meperidine, fentanyl, hydromorphone, oxymorphone, oxycodone, hydrocodone, methadone, propoxyphene, pentazocine, levorphanol, codeine, acetaminophen or combinations of these analgesics and the stool softener may be docusate, poloxamer 188, psyllium, methylcellulose, carboxymethyl cellulose, polycarbophil, bisacodyl, castor oil, magnesium citrate, magnesium hydroxide, magnesium sulfate, dibasic sodium phosphate, monobasic sodium phosphate, sodium biphosphate or combinations of these compounds.

In one preferred embodiment, the pharmaceutical composition comprises between about 10 mg to about 300 mg of docusate. In further embodiments of the invention, the pharmaceutical composition comprises between about 25 mg and about 200 mg, or between about 50 mg and about 100 mg of docusate.

In another preferred embodiment, the pharmaceutical composition comprises between about 0.10 grams to about 10.0 grams of psyllium. In further embodiments of the invention, the pharmaceutical composition comprises between about 0.25 grams and about 2 grams, or between about 0.5 grams and about 5 grams of psyllium.

In yet another embodiment, the pharmaceutical composition includes one or more pharmaceutically acceptable inert excipients. In a preferred embodiment, the single oral dosage form used in the method also contains acetaminophen, and in another embodiment, the dosage form containing these medications is formulated in a sustained release carrier allowing the analgesics or stool softeners to be released over an extended time period when orally administered to a human patient. Preferably, the time period of sustained release of the analgesic is a period of about 8 to about 24 hours after being orally administered to a human patient.

Another embodiment of the present invention is a method of preventing constipation during analgesic use by the administration of a single oral dosage form comprising codeine and at least about 50 mg of docusate. In a preferred embodiment, the oral dosage form also contains a non-opioid analgesic such as acetaminophen, and may be formulated as a sustained or delayed release dosage form to release the analgesic or the stool softener over an extended time period following oral administration to a human patient.

DETAILED DESCRIPTION OF THE INVENTION

The present invention provides a pharmaceutical dosage form for the simultaneous administration of opiate analgesics and stool softeners. This allows the prescribing professional to direct the administration of opiate analgesics or combinations containing opiates without having to assure patient compliance with a regimen of co-administered stool softeners. This also provides a method of adjusting the dose of stool softener to match the patient's opiate ingestion without separate intervention by the prescriber or other health care professionals. This inclusion of a stool softener with an opiate also results in a pharmaceutical composition having reduced potential for abuse and diversion. Therefore, the present invention is directed to pharmaceutical compositions comprising an analgesic or analgesic combination and a stool softener.

The analgesic is typically an opiate, although combinations of opiates or opiates in combination with another analgesic such as acetaminophen or aspirin are combined in a pharmaceutical composition containing a stool softener. The analgesic includes at least one of morphine, meperidine, fentanyl, hydromorphone, oxymorphone, oxycodone, hydrocodone, methadone, propoxyphene, pentazocine, levorphanol or codeine. In an alternative embodiment, the analgesic includes at least one of morphine, meperidine, fentanyl, hydromorphone, oxymorphone, oxycodone, hydrocodone, methadone, propoxyphene, pentazocine, levorphanol, acetaminophen or combinations of these analgesics. As acetaminophen has been shown to have a synergistic analgesic activity with the opiate analgesics, the analgesic is preferably a combination of an opiate or opiate derivative and acetaminophen. One particularly preferred embodiment of the present invention is a pharmaceutical composition comprising hydrocodone, acetaminophen and a stool softener. Another preferred embodiment of the present invention is a pharmaceutical composition comprising oxycodone, acetaminophen and a stool softener.

In the embodiments of the present invention comprising acetaminophen, the acetaminophen is present in a range of between about 10 mg and about 2000 mg. Preferably, the acetaminophen is present in a range of about 50 mg to about 1000 mg per dosage form. More preferably, the acetaminophen is present in a range of about 325 mg to about 750 mg per dosage form. Most preferably, each dosage form includes about 500 mg of acetaminophen.

The amount of the opiate analgesic or analgesic combination contained in the pharmaceutical composition depends upon the analgesic chosen and whether the dosage form is to be formulated for immediate release or sustained release of the opiate or analgesic combination. For example, if morphine is the intended opiate, the morphine may be present in doses between about 10 mg and about 60 mg including, but not limited to, about 15 mg, about 20 mg, about 30 mg and about 40 mg. Alternatively, the pharmaceutical composition may be formulated to include between about 30 mg to about 60 mg of morphine in a slow-release tablet or capsule. If meperidine is chosen as the analgesic or a member of the analgesic combination, the meperidine may be present in doses ranging from about 50 mg to about 100 mg. If fentanyl is chosen as the analgesic or a member of the analgesic combination, the fentanyl may be present in doses equivalent to doses ranging from about 200 μg, to about 1600 μg including about 400 μg, about 600 μg, about 800 μg, about 1200 μg of fentanyl base. If hydromorphone is chosen as the analgesic or a member of the analgesic combination, the hydromorphone may be present in doses ranging from about 1 mg to about 5 mg of hydromorphone. If oxymorphone is chosen as the analgesic or a member of the analgesic combination, the oxymorphone may be present in doses ranging from about 1 mg to about 10 mg. If oxycodone is chosen as the analgesic or a member of the analgesic combination, the oxycodone may be present in doses ranging from about 5 mg to about 20 mg. If hydrocodone is chosen as the analgesic or a member of the analgesic combination, the hydrocodone may be present in doses ranging from about 2.5 mg to about 15 mg, including, but not limited to, about 5 mg, about 7.5 mg and about 10 mg. If methadone is chosen as the analgesic or a member of the analgesic combination, the methadone may be present in doses ranging from about 5 mg to about 10 mg. If propoxyphene is chosen as the analgesic or a member of the analgesic combination, the propoxyphene may be present in doses ranging from about 32 mg to about 65 mg of the hydrochloride salt or from about 50 mg to about 100 mg of the napsylate salt. If pentazocine is chosen as the analgesic or a member of the analgesic combination, the pentazocine may be present in doses including, but not limited to, about 50 mg pentazocine base or doses of a pharmaceutically-acceptable salt of pentazocine approximately equivalent to about 50 mg of pentazocine base. If levorphanol is chosen as the analgesic or a member of the analgesic combination, the levorphanol may be present in doses including but not limited to about 2 mg of levorphanol tartrate. If codeine is chosen as the analgesic or a member of the analgesic combination, the codeine may be present in doses including but not limited to doses of a pharmaceutically-acceptable salt of codeine approximately equivalent to a range from about 30 mg to about 60 mg of codeine phosphate or approximately equivalent to a range of about 15 mg, to about 60 mg of codeine sulfate.

The stool softener may be any orally-administered medication that acts to increase any indicator of stool softener efficacy including stool water content, total stool output and bowel movement frequency. Preferably, the stool softener acts to increase the water content of the stool thereby softening the stool and making it easier to pass. The stool softener is included in the pharmaceutical composition in a dosage that is therapeutically effective in softening the stool in the intended human or mammalian patient. The stool softener may be docusate, poloxamer 188, psyllium, methylcellulose, carboxymethyl cellulose, polycarbophil, bisacodyl, castor oil, magnesium citrate, magnesium hydroxide, magnesium sulfate, dibasic sodium phosphate, monobasic sodium phosphate, sodium biphosphate or combinations of these compounds. The preferred stool softeners are psyllium and docusate.

In one embodiment of the present invention, the stool softener is psyllium present in a range of between about 0.1 gram and about 10.0 grams per dosage form. Preferably, the psyllium is present in a range of about 0.25 grams to about 2 grams per dosage form. More preferably, the psyllium is present in a range of about 0.3 grams to about 0.75 grams per dosage form. Most preferably, each dosage form includes about 0.5 grams of psyllium. For example, in one preferred embodiment of the present invention, the pharmaceutical composition comprises codeine present as either about 30 mg or about 60 mg of codeine phosphate, about 325 mg of acetaminophen and about 0.5 grams of psyllium.

In another embodiment of the present invention, the stool softener is docusate present in the composition as any salt of dioctyl sodium sulphosuccinate including the sodium and calcium salt. The term docusate is used herein to refer to dioctyl sodium sulphosuccinate and any pharmaceutically-acceptable salt thereof. In one embodiment of the present invention, the docusate is present in a range of between about 10 mg and about 300 mg per dosage form. Preferably, the docusate is present in a range of about 25 mg to about 200 mg per dosage form. More preferably, the docusate is present in a range of about 50 mg to about 100 mg per dosage form. Most preferably, each dosage form includes about 50 mg of docusate. For example, in one preferred embodiment of the present invention, the pharmaceutical composition comprises codeine present as either about 30 mg or about 60 mg of codeine phosphate, about 325 mg of acetaminophen and about 50 mg of docusate.

If poloxamer 188 is the intended stool softener, the poloxamer 188 is preferably present in doses that range between about 100 mg and about 400 mg including, but not limited to, about 200 mg. If methylcellulose is chosen as the stool softener, the methylcellulose is preferably present in doses ranging from about 1 gram to about 6 grams. If carboxymethylcellulose is chosen as the stool softener, the carboxymethylcellulose is preferably present in doses ranging between about 1 gram and about 6 grams. If polycarbophil is chosen as the stool softener, the polycarbophil is preferably included in doses that range from about 0.5 gram to about 6 grams. If bisacodyl is chosen as the stool softener, the bisacodyl is preferably included in doses ranging from about 5 mg to about 15 mg. If castor oil is chosen as the stool softener, the castor oil is preferably included in doses ranging from about 1 ml to about 60 ml. If magnesium sulfate is chosen as the stool softener, the magnesium sulfate is preferably included in doses ranging from about 2.5 grams to about 30 grams. If magnesium hydroxide is chosen as the stool softener, the magnesium hydroxide is preferably included in doses ranging from about 0.4 gram to about 4.8 grams. If magnesium citrate is chosen as the stool softener, the magnesium citrate is preferably included in doses ranging from about 2.5 grams to about 18 grams. If dibasic sodium phosphate is chosen as the stool softener, the dibasic sodium phosphate is preferably included in doses ranging from about 500 mg to about 3.8 grams. If monobasic sodium phosphate is chosen as the stool softener, the monobasic sodium phosphate is preferably included in doses ranging from about 2.0 grams to about 17 grams. If sodium biphosphate is chosen as the stool softener, the sodium biphosphate is preferably included in doses ranging from about 2.5 grams to about 20 grams.

When employed as pharmaceutical compositions, the analgesic and stool softener combinations of the present invention are usually administered orally. Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion. Such compositions are prepared in a manner well known in the pharmaceutical art and comprise at least one active compound.

This invention also includes pharmaceutical compositions containing the analgesic and stool softener active ingredients described above associated with pharmaceutically-acceptable carriers. In making the compositions of this invention, the active ingredients are usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the pharmaceutical compositions of the present invention can be in the form of oral solutions, syrups, soft and hard gelatin capsules and sterile packaged powders.

In preparing a formulation, it may be necessary to mill the active ingredients to provide the appropriate particle size prior to combining with the other ingredients. If the active compounds are substantially insoluble, they are ordinarily milled to a particle size of less than 200 mesh. If an active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 10 mg to about 20 grams of active ingredients. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient. Preferably, the analgesic compounds and the stool softeners described above are typically employed at no more than about 95 weight percent of the pharmaceutical composition, more preferably no more than about 75 weight percent, with the balance being pharmaceutically inert carrier(s).

The active compounds are effective over a wide dosage ranges and are generally administered in pharmaceutically effective amounts. It will be understood, however, that the amount of the compounds actually administered will be determined by a physician, in the light of the relevant circumstances, including the condition to be treated, the analgesic to be administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredients are dispersed evenly throughout the composition so that the composition may be readily subdivided into equally effective unit dosage forms such as tablets or capsules. This solid preformulation is then subdivided into unit dosage forms of the type described above containing from, for example, about 0.1 to about 20 grams of the active ingredients of the present invention.

The tablets or capsules of the present invention may be coated or otherwise compounded to provide a dosage form affording the advantage of prolonged action. For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate as are known in the art. Thus, in one embodiment of the present invention, the pharmaceutical dosage form is prepared such that upon administration, the analgesic or analgesic combination is released from the dosage form for absorption while the stool softener is released in a slow, delayed or sustained-release manner. This may help to prevent diarrhea by slowing the exposure of the alimentary tract to the stool softener while simultaneously allowing substantially complete release and absorption of the pain reliever-analgesic combinations. In this way the entire dose of stool softener is released slowly over about 2 hours to about 12 hours. Preferably, the dosage is released over about 4 hours to about 8 hours. For example, in one preferred embodiment of the present invention, the pharmaceutical dosage form comprises hydrocodone and acetaminophen prepared for immediate release following administration and docusate formulated for sustained release over about 4 hours to about 12 hours or over about 4 hours to 24 hours.

In another embodiment of the present invention, the pharmaceutical composition is formulated to release both the analgesic and the stool softener in a sustained release manner. This is particularly effective when the administration of a sustained release opiate or opiate combination is desired in instances of chronic pain treatment. For example, one preferred embodiment of the present invention a pharmaceutical composition formulated to contain oxycodone and docusate in a sustained release dosage form designed to release oxycodone and docusate over about 4 hours to about 16 hours. More preferably, this dosage form is designed to release the oxycodone and docusate over about 8 hours to about 12 hours. In other specific embodiments, the analgesic, or stool softener, or both can be released between about 4 and 16 hours, or between about 8 and 24 hours.

The liquid forms in which the compositions of the present invention may be incorporated for administration include aqueous solutions, suitably flavored syrups, oil suspensions and flavored emulsions with edible oils such as cottonseed oil, sesame oil, coconut oil, or peanut oil as well as elixirs and similar pharmaceutical vehicles.

Another embodiment of the present invention provides a method of preventing constipation in a patient receiving or in need of opiate analgesic therapy by the co-administration of a stool softener with the chosen opiate. The method encompasses the oral administration of any one of the pharmaceutical compositions of the present invention described above. The administration may continue for only a short time in the case of an acute condition requiring opiate therapy or for long periods in the case of conditions requiring chronic use of opiate analgesics. The dosing is dependent upon the condition being treated, the patient's individual perception of pain and the use of the opiate on a set time schedule as a prophylactic to prevent the onset of pain or on an as needed basis in response to perceived pain. Ultimately however, the individual dosing will be assessed by the prescribing professional evaluating the patient, the condition treated, the analgesic to be used, diet and the expected duration of therapy. As noted in the Example 2 below, the administration of opiates with a stool softener may increase systemic absorption of the stool softener and slow absorption of the analgesic. For this reason, the prescriber may recommend taking the compositions of the present invention on an empty stomach or with food depending on the desired onset of the analgesic effect.

Additional objects, advantages, and novel features of this invention will become apparent to those skilled in the art upon examination of the following examples thereof, which are not intended to be limiting.

EXAMPLES

Example 1

This example provides pharmacokinetic bioavalability data for opiate and analgesic medication orally administered in the presence of docusate and demonstrates a minimal effect of coadministration of docusate on the bioavialability of the opiate and analgesic. The study is a comparative, randomized, single-dose, 4-way pilot crossover bioavailability study of 500/10 mg acetaminophen/hydrocodone tablets and 50 mg docusate capsules in healthy adults under fed and fasting conditions. The objective of this pilot study was to assess whether docusate is absorbed in measurable amounts, the effect of docusate on acetaminophen and hydrocodone pharmacokinetics and the effect of food on all analytes. A total of 12 subjects, 5 males and 7 females, were enrolled in the study, and 10 subjects, 4 males and 6 females, completed the study.

In each period, subjects were housed from at least 10 hours before dosing until after the 12-hour draw. Subjects were required to fast overnight before dosing and for at least 4 hours thereafter. Subjects randomized to treatments C and D were in the fed state having started a standard breakfast 30 minutes prior to dosing. Subjects randomized to Treatments A and B were in a fasted state following a 10-hour overnight fast. Water was not permitted from 1 hour before until 1 hour after dosing, but was allowed at all other times. Standard meals were provided at approximately 4 and 9 hours after dosing, and at appropriate times thereafter. During housing, post-dose meal plans were identical for all periods. Subjects underwent four separate treatments as follows:

Treatment A: Subjects received a single oral dose of one 10 mg/500 mg Lortab® tablet and one 50 mg Colace® capsule taken with 240 mL of water under fasting conditions.

Treatment B: Subjects received a single oral dose of one 10 mg/500 mg Lortab® tablet taken with 240 mL of water under fasting conditions.

Treatment C: Subjects received a single oral dose of one 10 mg/500 mg Lortab® tablet and one 50 mg Colace® capsule taken with 240 mL of water 30 minutes after the start of a standard breakfast.

Treatment D: Subjects received a single oral dose of one 10 mg/500 mg Lortab® tablet taken with 240 mL of water 30 minutes after the start of a standard breakfast. There was a seven-day washout interval between each dose administration.

Blood samples were collected form each subject at the times listed in Table 1.

TABLE 1

| Analyte | Blood Sampling Schedule (hours) | | | | | | | | | | | | | |
|---|---|---|---|---|---|---|---|---|---|---|---|---|---|---|
| | 0 | 0.25 | 0.5 | 0.67 | 0.83 | 1 | 1.33 | 1.66 | 2 | 3 | 4 | 6 | 8 | 12 |
| Acetaminophen | x | x | x | X | x | x | x | x | x | x | x | x | x | x |
| Hydrocodone/ Hydromorphone | x | | x | | x | x | x | x | x | x | x | x | x | x |
| Docusate | x | x | x | | x | | | | x | | x | | x | |

Acetaminophen, hydrocodone and hydromorphone in plasma were analyzed using validated LC/MS/MS methods. Docusate in plasma was analyzed using a non-validated LC/MS/MS method. All samples were analyzed under non-GLP conditions. The analytical ranges were as follows: Acetaminophen: 50.0–30000.0 ng/mL; Hydrocodone: 0.500–150.000 ng/mL; Hydromorphone: 0.100–20.000 ng/mL; Docusate: 0.5–500 ng/mL. Docusate concentrations above the upper LOQ of 500 ng/mL correspond to extrapolated values. Due to the low number of samples taken for docusate it was necessary to estimate the corresponding kel values with two points in most cases. The AUC 0-t, AUCinf, AUC/AUCinf, Cmax, tmax, half-life and kel pharmacokinetic parameters were calculated for plasma acetaminophen, hydrocodone, hydromorphone and docusate. The results presented in Tables 2 and 3 address whether docusate is absorbed in measurable amounts and the effect of docusate on acetaminophen and hydrocodone pharmacokinetics. The effect of docusate on hydromorphone pharmacokinetics was also assessed.

The A/B comparisons in Tables 3 and 4 correspond to assessments under fasting conditions while the C/D comparisons correspond to assessments under fed conditions.

TABLE 2

| Analyses of Variance (ANOVA) Parameters | Least-Squares Means (LSM) | | | | Ratio of LSM | | 90% Confidence Interval | |
|---|---|---|---|---|---|---|---|---|
| | Form A | Form B | Form C | Form D | (A/B) (%) | (C/D) (%) | (A/B) (%) | (C/D) (%) |
| Acetaminophen in Plasma | | | | | | | | |
| AUC 0-t (ng · h/mL) | 21007.48 | 20720.60 | 19652.06 | 19545.72 | 101.4 | 100.5 | 96.7–106.2 | 96.1–105.2 |
| AUCinf (ng · h/mL) | 22653.46 | 22004.82 | 21473.77 | 21409.72 | 102.9 | 100.3 | 98.7–107.4 | 96.2–104.6 |
| Cmax (ng/mL) | 5452.473 | 5924.279 | 3940.379 | 4023.527 | 92.0 | 97.9 | 80.2–105.7 | 85.8–111.8 |
| Hydrocodone in Plasma | | | | | | | | |
| AUC 0-t (ng · h/mL) | 135.35 | 132.00 | 142.12 | 145.99 | 102.5 | 97.4 | 96.3–109.1 | 91.7–103.4 |
| AUCinf (ng · h/mL) | 162.06 | 151.17 | 170.22 | 174.74 | 107.2 | 97.4 | 100.0–114.9 | 91.4–103.8 |
| Cmax (ng/mL) | 24.28794 | 24.24384 | 22.26302 | 22.94215 | 100.2 | 97.0 | 89.5–112.1 | 87.1–108.1 |

TABLE 3

| Analyses of Variance (ANOVA) Parameters | Least-Squares Means (LSM) | | | | Ratio of LSM | | 90% Confidence Interval | |
|---|---|---|---|---|---|---|---|---|
| | Form A | Form B | Form C | Form D | (A/B) % | (C/D) % | (A/B) % | (C/D) % |
| Hydromorphone in Plasma | | | | | | | | |
| AUC 0-t (ng · h/mL) | 6.5433 | 7.1075 | 6.3270 | 6.2051 | 92.1 | 102.0 | 85.0–99.7 | 94.5–110.0 |
| AUCinf (ng · h/mL) | 10.2390 | 10.9436 | 10.9046 | 10.9575 | 93.6 | 99.5 | 84.4–103.8 | 89.2–111.0 |
| Cmax (ng/mL) | 0.96508 | 0.99512 | 0.74228 | 0.74216 | 97.0 | 100.0 | 86.8–108.3 | 90.0–111.2 |
| Docusate in Plasma | | | | | | | | |
| AUC 0-t (ng · h/mL) | 1171.94 | N/A | 1455.68 | N/A | N/A | N/A | N/A | N/A |
| AUCinf (ng · h/mL) | 1171.31 | N/A | 1508.26 | N/A | N/A | N/A | N/A | N/A |
| Cmax (ng/mL) | 608.14244 | N/A | 634.74354 | N/A | N/A | N/A | N/A | N/A |

Measurable docusate concentrations were observed throughout the period of blood sampling. Hence, it may be concluded that docusate is absorbed in measurable amounts.

(Lortab®+Colace®) while the D/B comparisons correspond to assessments for acetaminophen and hydrocodone (Lortab®) administered alone.

TABLE 4

| Analyses of Variance (ANOVA) | Least-Squares Means (LSM) | | | | Ratio of LSM | | 90% Confidence Interval | |
|---|---|---|---|---|---|---|---|---|
| Parameters | Form A | Form B | Form C | Form D | (C/A) % | (D/B) % | (C/A) % | (D/B) % |
| Acetaminophen in Plasma | | | | | | | | |
| AUC 0-t (ng · h/mL) | 21007.48 | 20720.60 | 19652.06 | 19545.72 | 93.5 | 94.3 | 89.3–98.0 | 90.2–98.7 |
| AUCinf (ng · h/mL) | 22653.46 | 22004.82 | 21473.77 | 21409.72 | 94.8 | 97.3 | 90.7–99.0 | 93.5–101.3 |
| Cmax (ng/mL) | 5452.473 | 5924.279 | 3940.379 | 4023.527 | 72.3 | 67.9 | 62.9–83.0 | 59.5–77.5 |
| Hydrocodone in Plasma | | | | | | | | |
| AUC 0-t (ng · h/mL) | 135.35 | 132.00 | 142.12 | 145.99 | 105.0 | 110.6 | 98.6–111.8 | 104.2–117.4 |
| AUCinf (ng · h/mL) | 162.06 | 151.17 | 170.22 | 174.74 | 105.0 | 115.6 | 98.0–112.6 | 108.5–123.2 |
| Cmax (ng/mL) | 24.28794 | 24.24384 | 22.26302 | 22.94215 | 91.7 | 94.6 | 81.9–102.6 | 85.0–105.4 |

TABLE 5

| Analyses of Variance (ANOVA) | Least-Squares Means (LSM) | | | | Ratio of LSM | | 90% Confidence Interval | |
|---|---|---|---|---|---|---|---|---|
| Parameters | Form A | Form B | Form C | Form D | (C/A) % | (D/B) % | (C/A) % | (D/B) % |
| Hydromorphone in Plasma | | | | | | | | |
| AUC 0-t (ng · h/mL) | 6.5433 | 7.1075 | 6.3270 | 6.2051 | 96.7 | 87.3 | 89.3–104.7 | 80.9–94.2 |
| AUCinf (ng · h/mL) | 10.2390 | 10.9436 | 10.9046 | 10.9575 | 106.5 | 100.1 | 95.3–119.1 | 90.6–110.6 |
| Cmax (ng/mL) | 0.96508 | 0.99512 | 0.74228 | 0.74216 | 76.9 | 74.6 | 68.9–85.9 | 67.1–82.9 |
| Docusate in Plasma | | | | | | | | |
| AUC 0-t (ng · h/mL) | 1171.94 | N/A | 1455.68 | N/A | 124.2 | N/A | 112.8–136.8 | N/A |
| AUCinf (ng · h/mL) | 1171.31 | N/A | 1508.26 | N/A | 128.8 | N/A | 109.1–151.9 | N/A |
| Cmax (ng/mL) | 608.14244 | N/A | 634.74354 | N/A | 104.4 | N/A | 72.4–150.4 | N/A |

Correspondingly, it was possible to calculate pharmacokinetic parameters for docusate. It should be noted, however, that the pharmacokinetic parameters have not been robustly assessed as there were only 7 samples collected for docusate analysis.

To assess the effect of docusate on the pharmacokinetics of acetaminophen, hydrocodone and hydromorphone, ratios of least squares means and 90% confidence intervals for the difference between drug formulation LSMs were derived from the analyses on the ln-transformed pharmacokinetic parameters AUC 0-t, AUCinf and Cmax. The comparisons of interest were A versus B (fasted conditions) and C versus D (fed conditions). For all analytes under both fasted and fed conditions, the ratios of least squares means and corresponding 90% confidence intervals fall within the range of 80–125%. It should also be noted that docusate has the effect of delaying tmax by approximately 30 minutes for all analytes under both fasted and fed conditions. However, from these results it is concluded that docusate has no significant effect on the pharmacokinetics of acetaminophen, hydrocodone or hydromorphone under fed and fasted conditions.

Example 2

This example demonstrates the affect of food on the pharmacokinetics of acetaminophen, hydrocodone, hydromorphone and docusate in subjects under the clinical conditions described in Example 1. In Table 4 and Table 5, the C/A comparisons correspond to assessments for docusate co-administered with acetaminophen and hydrocodone Ratios of least squares means and 90% confidence intervals for the difference between drug formulation LSMs were derived from the analyses on the ln-transformed pharmacokinetic parameters AUC 0-t, AUCinf and Cmax. The comparisons of interest were C versus A (Lortab® and Colace® co-administered) and D versus B (Lortab® administered alone).

For acetaminophen and hydromorphone, the ratio of least-squares means and 90% confidence intervals derived from the analysis of the ln-transformed parameters AUC 0-t and AUCinf were within the 80–125% range for both the C versus A and D versus B comparisons. However, the corresponding ratios of least-squares means and 90% confidence intervals for the ln-transformed Cmax parameter were not within this range. In addition, it is apparent that food delays the tmax by approximately 1 hour for acetaminophen and by approximately 2 hours for hydromorphone. Based on these results, it may be concluded that food has the effect of lowering the Cmax and delaying tmax for both acetaminophen and hydromorphone but does not affect the extent of exposure, as measured by the AUC parameters.

For hydrocodone, the ratio of least-squares means and 90% confidence intervals derived from the analysis of the ln-transformed parameters AUC 0-t, AUCinf and Cmax were within the 80–125% range for both the C versus A and D versus B comparisons. In addition, food appears to delay tmax for hydrocodone by approximately 1 hour. It should be noted that in the D versus B comparison (Lortab® administered alone), the analysis of the ln-transformed AUCinf parameter yielded a ratio of least squares means of 115.6%.

This suggests that food tends to slightly increase the extent of exposure of hydrocodone. Nevertheless, it may be generally concluded that food has no significant effect on the rate (Cmax) or the extent (AUC) of exposure of hydrocodone.

For docusate, the ratio of least-squares means derived from the analysis of the ln-transformed parameters AUC 0-t and Cmax are within the 80–125% range while the corresponding 90% confidence intervals were not within this range. In the case of the analysis of the ln-transformed parameter AUCinf for docusate, the ratio of least-squares means and 90% confidence interval were not within the 80–125% range. In addition, food appears to delay tmax for docusate by approximately 30 minutes. Based on these results it may be concluded that food tends to increase the extent of exposure (AUC) of docusate. In the case of Cmax, while it is noted that the 90% confidence interval is not within the 80–125% range, the ratio of least-squares means of 104.5% may suggest that the rate of exposure of docusate is not significantly affected by food.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A mono-phasic pharmaceutical composition suitable for single dose administration for reducing the risk of constipation caused by the administration of an opioid analgesic consisting of:

about 2.5 mg/dose to about 15 mg/dose of hydrocodone;
   about 10 mg/dose to about 2000 mg/dose of acetaminophen;
   a stool softener selected from the group consisting of about 50 mg/dose to about 100 mg/dose of docusate and about 100 mg/dose to about 400 mg/dose of poloxamer 188; and,
   a pharmaceutically acceptable carrier.

2. The pharmaceutical composition of claim 1, wherein the acetaminophen is present in about 50 mg/dose to about 1000 mg/dose of acetaminophen and the stool softener is present in about 50 mg/dose to about 100 mg/dose of docusate.

3. The pharmaceutical composition of claim 1, wherein the acetaminophen is present in about 325 mg/dose to about 750 mg/dose of acetaminophen and the stool softener is present in about 50 mg/dose to about 100 mg/dose of docusate.

4. The pharmaceutical composition of claim 3, wherein the composition contains about 325 mg/dose of acetaminophen and about 50 mg/dose of docusate.

5. The pharmaceutical composition of claim 3, wherein the composition contains about 325 mg/dose of acetaminophen and about 100 mg/dose of docusate.

6. The pharmaceutical composition of claim 1, wherein the acetaminophen is present in about 50 mg/dose to about 1000 mg/dose of acetaminophen and the stool softener is present in about 100 mg/dose to about 400 mg/dose of poloxamer 188.

7. The pharmaceutical composition of claim 1, wherein the composition contains about 325 mg/dose to about 750 mg/dose of acetaminophen and the stool softener is present in about 100 mg/dose to about 400 mg/dose of poloxamer 188.

8. The pharmaceutical composition of claim 7, wherein the composition contains about 325 mg/dose of acetaminophen and about 200 mg/dose of poloxamer 188.

* * * * *